United States Patent [19]

Cui et al.

[11] Patent Number: 5,451,526
[45] Date of Patent: Sep. 19, 1995

[54] DETERMINATION OF OXIDANT OR REDUCTANT CONCENTRATION BY THE SPECTROPHOTOMETRIC OR VISUAL RESPONSE IN OXIDATION OR REDUCTION OF POLYANILINE

[75] Inventors: Cheng Q. Cui; Yu L. Huang; Jim Y. Lee, all of Singapore, Singapore

[73] Assignee: National University of Singapore, Singapore, Singapore

[21] Appl. No.: 197,257

[22] Filed: Feb. 16, 1994

[51] Int. Cl.$^6$ ............... G01N 33/02; G01N 33/14
[52] U.S. Cl. ............... 436/164; 436/93; 436/127; 436/138; 436/169; 436/904
[58] Field of Search ............... 436/63, 100, 102, 93, 436/127, 138, 164, 169, 171, 904

[56] References Cited

U.S. PATENT DOCUMENTS 3,845,030  7/1989  Batz et al. ............... 435/28
4,141,688  2/1979  Morris et al. ............... 23/230 B

FOREIGN PATENT DOCUMENTS 4351949  12/1992  Japan .

OTHER PUBLICATIONS

Batich, C. D. "Chromatic Changes in Polyaniline Film", J. Electrochem. Soc. vol. No. 3 Mar. 1990 883–885.
M. Olliver, 1 *The Vitamins,* 359–367 (1967).
Nagy et al., 31 Life Sciences, vol. 31, 2611–2616 (1982).
Schenck et al., 54 Anal. Chem., 1452–1454 (1982).
Brin, *Ascorbic Acid–Chemistry, metabolism and uses* 369–379 (1982).
Farmer et al., 34 Proc. Soc. Exp. Biol. Med, 146–161 (1936).
Roe et al., 147, *J. Biol. Chem.,* 399–407 (1943).
Grote et al., 212 *Anal. Chem. Acta,* 273–278 (1988).
Tillmans, 54 *Z. Unters. Lebensm,* 33–38 (1980).
Leonhardt et al., 122 *Z. Anal Chem.* 3–10 (1941).
Sastry et al., 19 *Talanta,* 212–220 (1972).
Leinweber et al., "Methods in Enzymology", 143, 15–17 (1987).
Smith, 59, Anal. Chem, 2256–2259 (1987).
Llyod et al., 28 Food Chemistry, 157–268 (1988).
Sidwell et al., 2, *Biosensors,* 221–238 (1986).
Carvalho et al., Process Biochemistry, 52–54 (Apr. 1989).
"Methods of Biochemical Analysis and Fodd Analysis", Boehringer Mannheim, 1989, pp. 18–20.
"Measurement of Dissolved Oxygen", Hitchman et al., Chemical Analysis, vol. 49, 1978, pp. xiii–191.

*Primary Examiner*—David A. Redding
*Attorney, Agent, or Firm*—Birch, Stewart, Kolasch & Birch

[57] ABSTRACT

The present invention is directed to a method for determining the presence of an oxidant or reductant in a sample by contacting the sample with a thin film of polyaniline in the reduced state or oxidized state, respectively, and measuring the color change occurring with the oxidation or reduction, respectively, of the polyaniline film.

14 Claims, 13 Drawing Sheets

(A-0.169)

(A-0.129)

DETERMINATION OF OXIDANT OR REDUCTANT CONCENTRATION BY THE SPECTROPHOTOMETRIC OR VISUAL RESPONSE IN OXIDATION OR REDUCTION OF POLYANILINE

BACKGROUND OF THE INVENTION

1. Field of the Invention

The present invention is directed to the use of polyanilines, which undergo a color change upon oxidation or reduction, in the visual or spectrophotometric determination of the presence of oxidants or reductants in a sample.

2. Description of the Related Art

L-Ascorbic acid (vitamin C) occurs naturally in many foodstuffs (fruits, vegetables, dairy products, meat, etc.) and is frequently added to processed foods as an antioxidant. The production of ascorbic acid from fermentation is an important bioprocess which supplies most of the demands of the pharmaceutical as well as the food industry for ascorbic acid. Determination of ascorbic acid is important, due to both its nutritional value as a vitamin and oxygen scavenger, as a freshness indicator and as a control parameter during fermentation (see 1M. Olliver, *The Vitamins* 359-367(W. H. Sebrell & R. S. Harris eds., 2d ed. 1967)). Measurement of ascorbic acid levels in clinical samples (urine, blood, etc.) is also of interest, since ascorbic acid concentration is a useful indicator of several pathological states (see Nagy et al., 31 *Life Sci.* 2611-2616(1982); Schenk et al., 54 *Anal. Chem.* 1452-1454(1982); M. Brin, *Ascorbic Acid: Chemistry, metabolism, and uses* 369-379(P. A. Seib & B. M. Tolbert eds., 1982)).

Ascorbic acid is a moderately strong reducing agent in aqueous media ($E_{\frac{1}{2}} = -0.104$ V vs SCE at pH 5) (see Leinweber et al., 143 *Methods Enzymol.* 15-17(1987). Most analytical methods exploit its ease of oxidation, and deduce its concentration by spectrophotometric determination (see Farmer, 34 *Proc. Soc. Exp. Biol. Med.* 146-160(1936); Roe et al., 147 *J. Biol. Chem.* 399-407(1943); and Grote et al., 212 *Anal. Chim. Acta* 273-278 (1988)) or titration (see Tillmans, 54 *Z. Unters. Lebensm.* 33-38(1972); Leonhardt et al., 122 *Z. Anal. Chem.* 3-10(1941); and Sastry et al., 19 *Talanta* 212-220(1972)) of the redox products. For example, the dye 2,6-dichlorophenolindophenol is often used as an oxidant in ascorbic acid determination, and its reduction is measured spectrophotometrically. An analytical problem occurs if other reductants of interest for foodstuffs, particularly sulfites, are also present in significant quantities in the ascorbic acid samples. In such cases the background noise from other reductants may constitute a large part of the total measurement. The indirect determination of ascorbic acid using biosensors based on immobilized ascorbate oxidase is the only reliable homogeneous assay (see Lloyd et al., 28*Food Chem.* 257-264(1988); Sidwell et al., 2 *Biosensors* 221-238(1986); and Carvallo et al., *Process Biochem.* 52-54(April, 1989)) besides the well established, but expensive and complicated HPLC method (see L-Ascorbinsaure, Boehringer Mannheim, *Methoden der biochemischen Analytik und Lebensmittelanalytik* 16-18(1987)). There are some application problems with the biological method as well. Firstly, ascorbic acid oxidase is an expensive enzyme (approximately $100/10 mg). Secondly, the inadequate stability of the enzyme, irrespective of the immobilization method, has always been a difficult problem in the development of biosensors. Lastly, the strongly reducing potential that is required for the operation of biosensors (approximately −0.94 V vs SCE) may lead to the co-reduction of background oxidants (see 49 M. L. Hitchman, *Chemical Analysis (P. J. Elving & J. D. Winefordner eds.,* 1978)). Therefore, there has been a need to develop a simple, and yet highly selective method for the determination of ascorbic acid.

SUMMARY OF THE INVENTION

It is an object of the present invention to provide a simple sensor made of polyaniline (PAn) which can be used to measure the levels of oxidants or reductants in practical samples by either spectrophotometry, or by visual comparison of the color change of the sensor to films of precalibrated colors, in the same way that paper indicators are used in the pharmaceutical industry.

It is a particular object of the present invention to provide a sensor which can be used to measure the amounts of ascorbic acid present in practical samples.

It is a further object of the invention to provide a PAn thin film sensor material that can be easily produced at low cost.

It is also an object of the invention to provide a sensor material wherein a single calibration curve can be provided by the manufacturer, thereby eliminating the need for calibration runs by the user of the sensor.

It is also an object of the present invention to provide a sensor which is durable, and can be used for a number of experimental runs.

It is also an object of the present invention to provide a sensor material that is easily storable, and which can be easily activated prior to use.

Finally, it is an object of the present invention to provide a sensor which will not suffer from interference from sulfite present in the sample.

These, and other objects of the present invention are obtained by providing a method for determining the presence of a reductant in a sample, comprising contacting said sample with a polyaniline in a partially oxidized state, reducing said polyaniline to a lower oxidation state, measuring the color change of said polyaniline accompanying said reduction, and determining the concentration of reductant present based upon said color change.

The reductant in the method described above is desirably ascorbic acid, the polyaniline in a partially oxidized state is desirably emeraldine, and polyaniline in a lower oxidation state is desirably leucoemeraldine.

The method of measuring of the color change may include spectrophotometric analysis of said color change, more particularly ultraviolet/visible light spectrophotometric analysis.

Alternatively, the method may include visually determining the reductant concentration based upon the variation in thickness of the PAn film that undergoes a definite color change in a prescribed time. For a given PAn film thickness, there is a color change within a prescribed time if the reductant (or oxidant) concentration is above a certain level, and no color change if the concentration is below this level. Measurement is made by comparison with a calibrated range of PAn films of various thicknesses that have undergone the color change in a prescribed time for various concentrations of reactant.

The sample to be analyzed may contain sulfites, and may be selected from the group consisting of urine samples, blood samples, food samples, pharmaceutical samples, and industrial waste samples. Desirably, the sample is a sample of a fruit juice.

The objects and advantages of the present invention is also obtained by providing a method for determining the presence of an oxidant in a sample, comprising contacting said sample with a polyaniline in a reduced state, oxidizing said polyaniline to a higher oxidation state, measuring the color change of said polyaniline accompanying said oxidation, and determining the concentration of said oxidant present based upon said color change.

In this case, the polyaniline in a reduced state is leucoemeraldine, and the polyaniline in a higher oxidation state is emeraldine.

Again, the color change may be measured by the spectrophotometric methods discussed above, or by the visual methods discussed above.

The sensor prepared according to the present invention can be easily mass produced at low cost, can be used with a single calibration curve provided by the manufacturer, and is usable over at least 50 experimental runs per sheet. The film forming the sensor is relatively stable in air, and can be stored in a dark room without controlling the atmosphere. The films are easily activated before measurement, and the interference of sulfite in the measurement is negligible.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

FIG. 11A shows a test strip using PAn layers of varying thicknesses. FIG. 11B shows a test strip using a single PAn layer formed as a wedge.

DETAILED DESCRIPTION OF THE INVENTION

Figure 1:
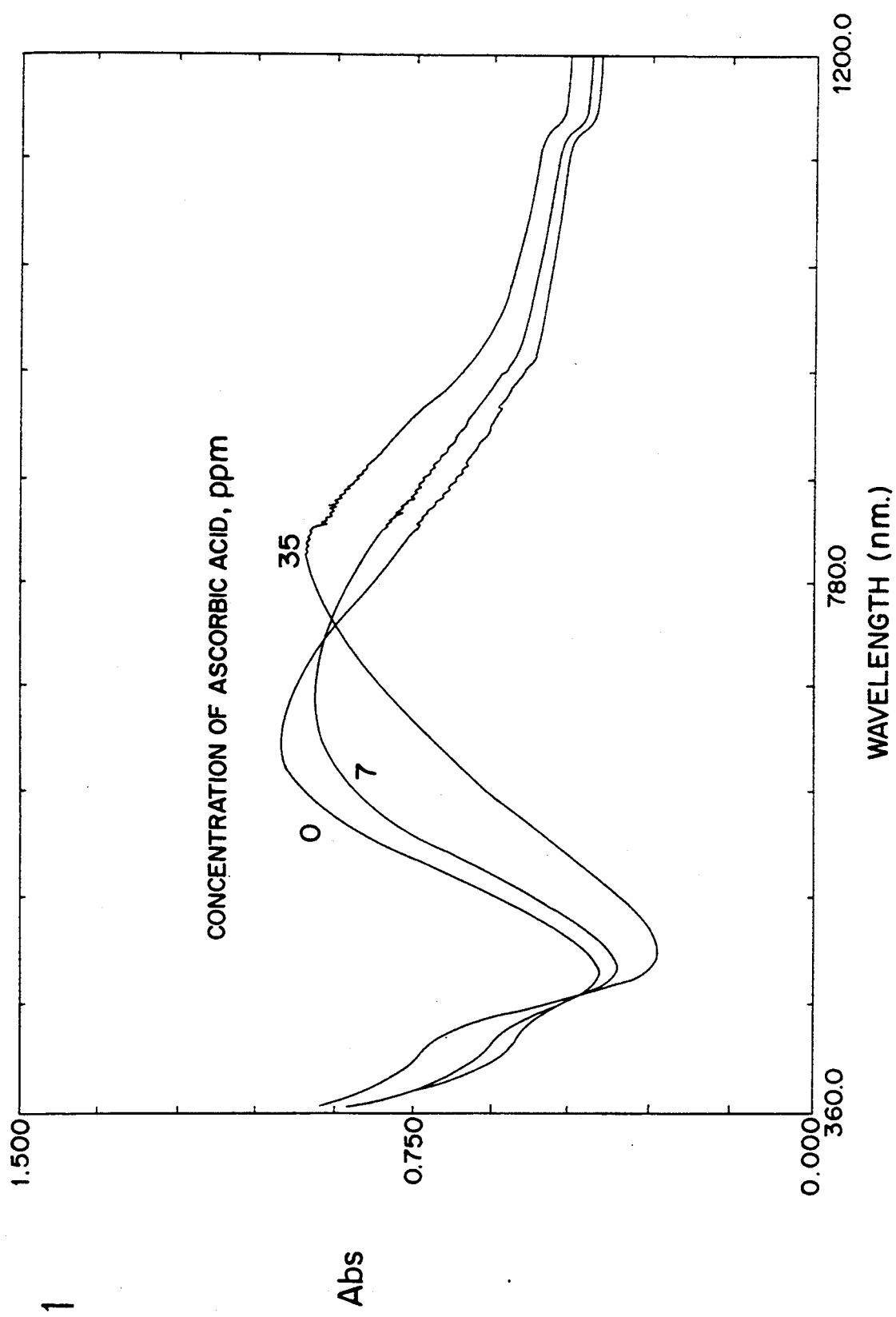
FIG. 1 shows UV/visible spectra of the thick electrochemically deposited PAn film (L3) in different concentrations of ascorbic acid.

Polyaniline (PAn) is commonly prepared in the partially oxidized state of emeraldine and can be easily reduced to the leucoemeraldine state. The reduction also brings about a color change from blue (in neutral solutions) or green (in acidic solutions) to light yellow. In neutral solutions PAn switches between these two oxidation states in the potential range of 0.012 to 0.326 V (vs SCE). As the reduction potential of PAn in the emeraldine form is more anodic than that of ascorbic acid at −0.104 V (vs SCE), the addition of ascorbic acid to a PAn film would reduce the latter from the blue emeraldine form to the light-yellow leucoemeraldine form. The color change of PAn film is most easily detected by UV/vis spectroscopy and can be related directly to the concentration of ascorbic acid in the solution.

The redox reaction between PAn and ascorbic acid can be categorically written as:

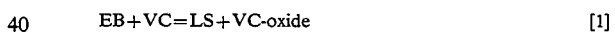

$$EB + VC = LS + VC\text{-oxide} \qquad [1]$$

where EB and LS are PAn in the emeraldine and leucoemeraldine states, respectively. VC and VC-oxide represent ascorbic acid and its oxidized form. The reaction is reversible under the experimental conditions, and is probably rate limited by the diffusion of ascorbic acid in the PAn film. The following rate expression was found to satisfactorily describe the kinetics of the system:

$$-d[EB]/dt = k([EB]) \times [VC]^o \qquad [2]$$

Integration of equation [2] leads to equation [3]

$$\ln[EB] = \ln[EB]_0 - k[VC]^o t \qquad [3]$$

where $[VC]^o$ is the concentration of ascorbic acid in the bulk of the solution and $[EB]_0$ the initial concentration of emeraldine. The emeraldine dine concentrations can be conveniently replaced by the absorbance value of PAn at a suitably chosen wavelength, i.e.,

$$[EB] \propto (A - A_\infty) \qquad [4]$$

$$[EB]_0 \propto (A_0 - A_{28}) \qquad [5]$$

where $A_0$ and $A_\infty$ are the respective absorbances at the beginning (t=0) and at the end (t=∞) of the reaction.

Equation [3] can then be rewritten as $$\ln(A-A_\infty) = \ln(A_0-A_\infty) - k[VC]^o t \quad [6]$$

From the last Equation, the rate of change of $\ln(A-A_\infty)$ with t, b, and the quantity $(A-A_{2B})$ at a constant reaction time of T, $(A_{T-A\infty})$, can be derived as:

$$b = d\ln(A-A_\infty)/dt = -k[VC]^o \quad [7]$$

$$\ln(A_T-A_\infty) = \ln(A_0-A_\infty) - kT[VC]o \quad [8]$$

As $A_0$ and $A_\infty$ are constants for a given PAn film, the slope in the semi-logarithmic plot of $(A-A_\infty)$ against time, $d\ln(A-A_\infty)/dt$, or the measurement of $\ln(A-A_\infty)$ for a constant reaction time of T are linear functions in the bulk concentration of ascorbic acid and as such are useful for the determination of the latter.

The procedure in this invention makes use of this property, and forms the basis of ascorbic acid determination by measurement of the spectrophotometric response of PAn reduction. The present invention is also applicable to the determination of other redox agents, such as sulfite in wine and alcohol, and dopamine in living brain tissues, uric acid, epinephrine, serotonin, tryptophan, tyrosine, and 3,4-dihydroxybenzylamine. In cases where the redox agent is an oxidant, the PAn film can be set in the reduced form prior to the measurement, and the color change from light-yellow to blue is used instead. Similarly, based on the reversibility of Reaction [1], the open-circuit potential of PAn film can also be used in lieu of the spectrophotometric determination of ascorbic acid.

The present invention may be further understood from the following non-limiting examples.

EXAMPLES

Aniline and ascorbic acid were of the AR grade (BDH). Aniline was further purified by distillation over zinc dust to remove oxidized impurities. In order to minimize the oxidation of ascorbic acid by dissolved oxygen, standard solutions of ascorbic acid were prepared from a fresh stock solution of the solid acid in oxygen-free deionized water which was kept only for 5 hours on the day of use.

Two methods, namely the electrochemical and chemical oxidation of aniline, were used for the preparation of PAn films.

Electrochemical deposition PAn film was potentiostatically deposited from 0.2M aniline in 1M $H_2SO_4$ at a potential of 0.8 V (vs SCE) on conductive indium tin-oxide glass plates ($1\times5$ cm$^2$). Various deposition times up to a total of 600 seconds were used. The films deposited were carefully rinsed with a copious amount of deionized water until a uniform adherent layer remained on the conductive glass. The deposit was then air dried and stored in a clean environment before use. Electrodeposited films having thicknesses corresponding to deposition times of 60 seconds (L2), 600 seconds (L3) and 1000 seconds (L4) were prepared according to this procedure. The L3 film is the film used in the examples unless stated otherwise.

Chemical deposition PAn was chemically deposited on a transparent film of poly(ethylene terephthalate) (PET) ($2\times5$ cm$^2$) from a 100 ml 1M $H_2SO_4$ solution containing 1 ml of aniline, 0.9 gm of $KIO_3$ and 1 gm of 5-sulfosalicylic acid. A deposition time of 2.5 hours at room temperature was used to produce the chemically synthesized film used in the examples. The PAn coating on both sides of the film was carefully washed to remove loose deposits. The film was dried, cut into sections of $1\times5$ cm$^2$ each, and stored in a clean environment before use.

UV/vis spectra were measured by using a Shimazu UV3100 spectrometer. Prior to every spectrophotometric measurement, the PAn film was equilibrated in an acidified $FeCl_3$ solution for 1 to 2 minutes to ascertain the presence of PAn in the emeraldine oxidation state. The oxidized PAn was then carefully washed with deionized water, and transferred quickly to the cuvette containing the ascorbic acid solution for spectrophotometric measurements.

FIG. 1 shows the UV/visible spectra of the thick electrodeposited PAn film (L3) in standard ascorbic acid solutions. In the absence of ascorbic acid, the most prominent absorption peak occurred at about 630 nm, showing a blue color. This is characteristic of the benzenoid-quinoid transition in the emeraldine form of PAn base. As the concentration of ascorbic acid in the standard solutions increased, the peak at approximately 630 nm displayed a red shift. In particular, the peak was displaced to approximately 870 nm when the ascorbic acid concentration reached 70 ppm. This observation corresponds to the reduction of emeraldine base by ascorbic acid according to Reaction [1], whereby the extent of reduction increases with the ascorbic acid concentration. More importantly, FIG. 1 shows that the absorbance at a fixed wavelength (for example, 630 nm) decreases with the increase in the concentration of ascorbic acid. This shows that the change in the chromatic property of PAn due to Reaction [1] can be used effectively as a measurement of ascorbic acid concentration.

Figure 2:
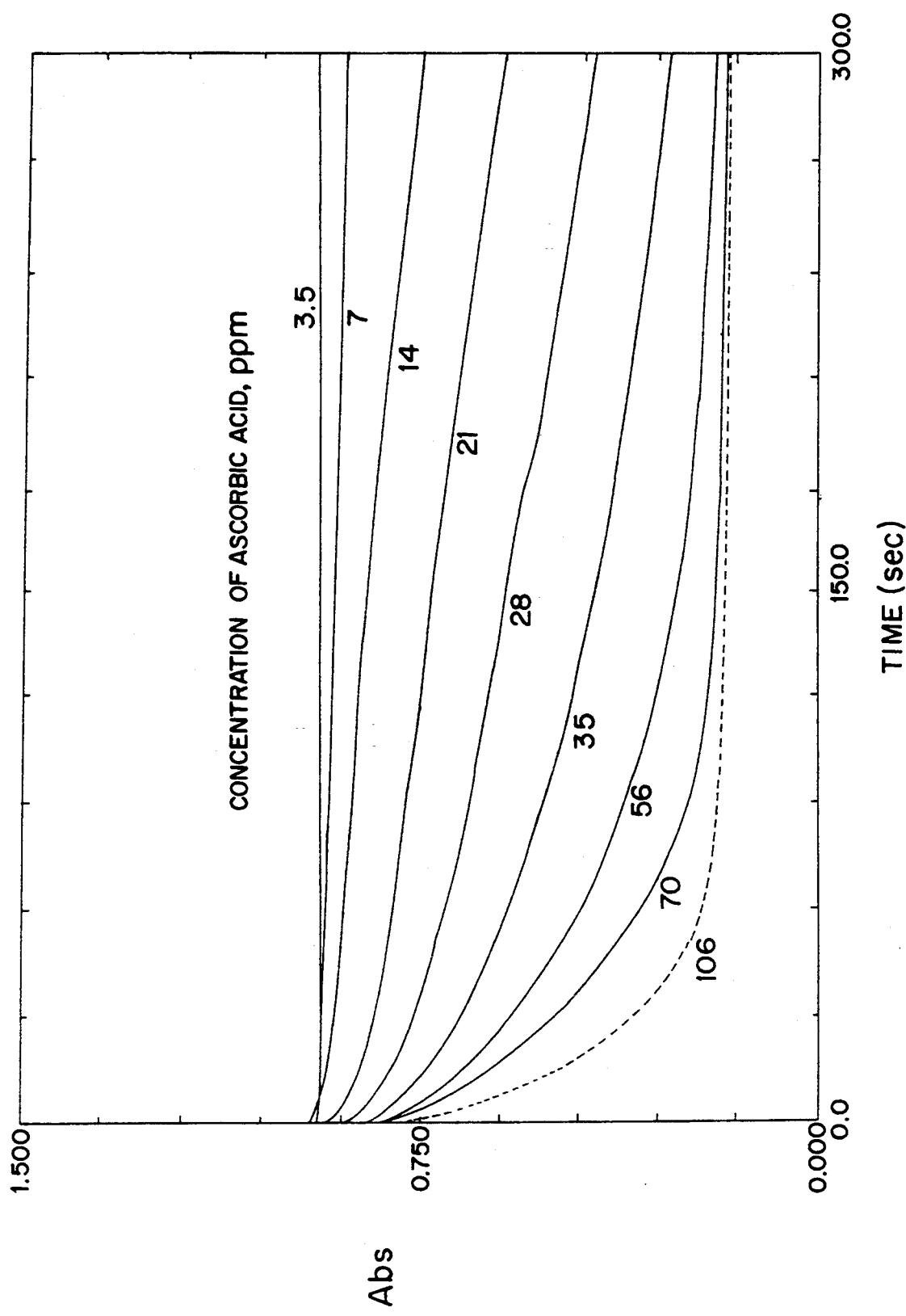
FIG. 2 shows the time course of UV/visible spectra of L3 PAn film in different concentrations of ascorbic acid.
Figure 3A:
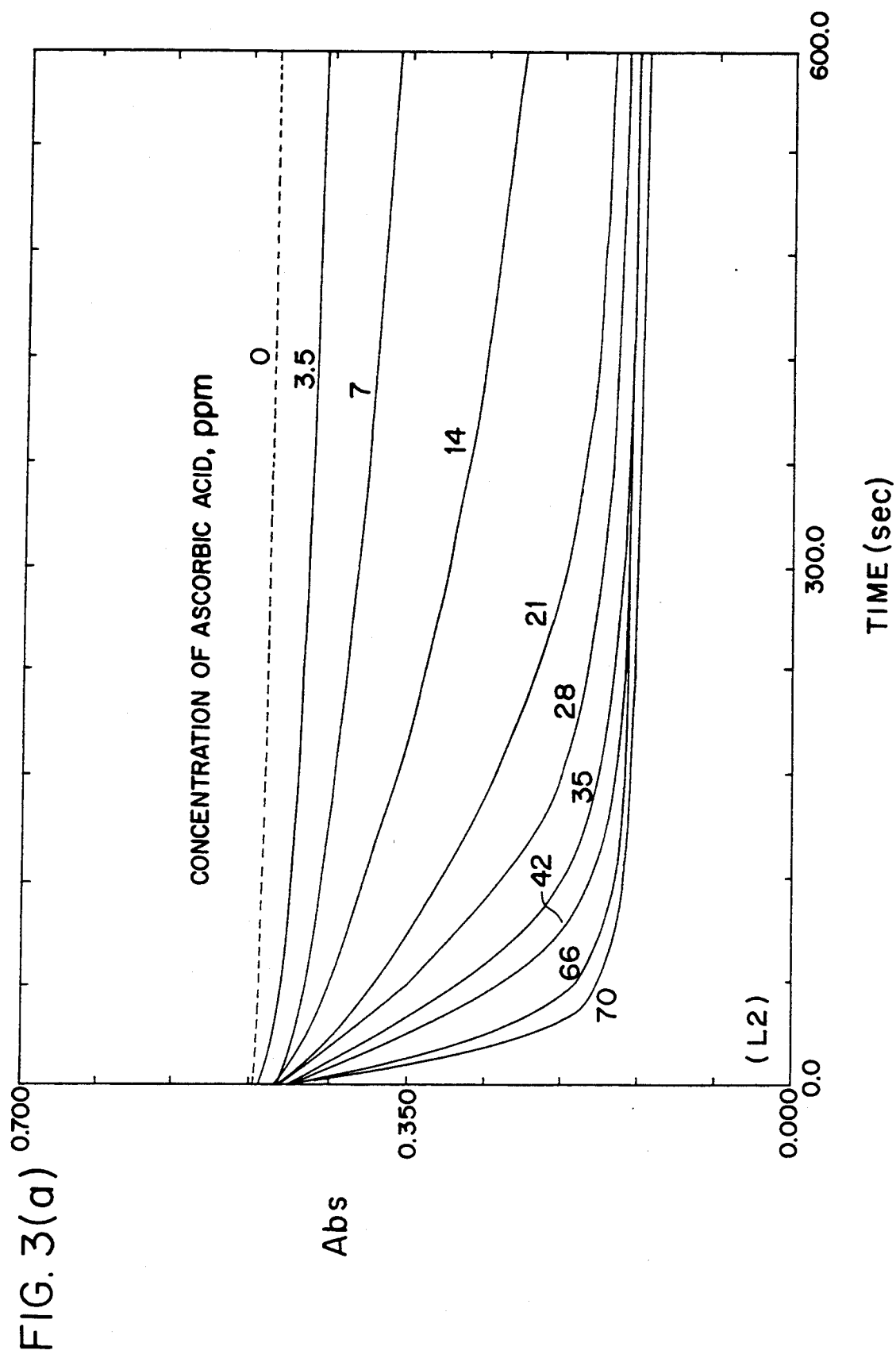
FIGS. 3a and 3b show the time course of UV/visible spectra of (a) the thin (L2) and (b) the very thick (L4) electrochemically deposited PAn film in different concentrations of ascorbic acid.
Figure 3B:
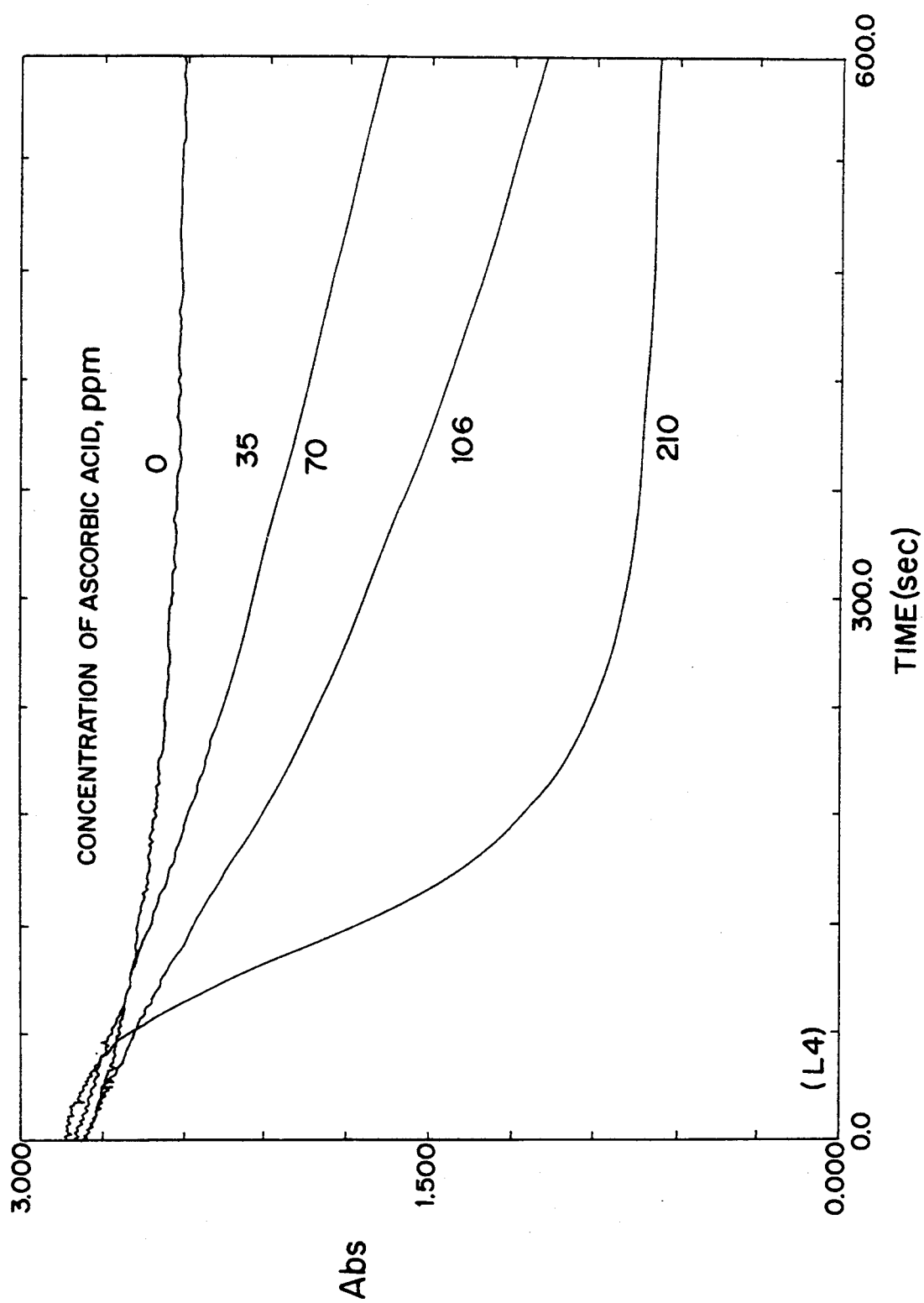

FIG. 2 shows the time course UV/vis spectra of the L3 PAn film in various concentrations of ascorbic acid. The measurement wavelength was fixed at 630 nm, corresponding to the peak of the benzenoid-quinone transition in pristine emeraldine. In the absence of ascorbic acid, the absorbance value was nearly time invariant, an indication that emeraldine base was stable in deionized water for the time required for such measurements. The absorbance in the absence of ascorbic acid was taken as $A_0$, which should parallel the amount of emeraldine base in the film. In the presence of ascorbic acid, however, the absorbance decreased sharply initially. This was followed by a more gradual decrease, leading finally to an equilibrium state within the measurement period, if the concentration of ascorbic acid was sufficiently high. The change in the absorbance could be rationalized in terms of the slower diffusion of ascorbic acid within the film. The initial decrease was rapid because it involved the reduction of the very accessible surface PAn. Subsequent reduction required the diffusive penetration of dissolved ascorbic acid into a solid film interior, a process that entailed much higher mass transfer resistance. Nevertheless, in the presence of a high ascorbic acid concentration, the emeraldine base was eventually fully reduced and the absorbance became constant. The constant absorbance value, $A_\infty$, due to background absorption from the fully reduced emeraldine, was dependent on the PAn film thickness. The quantity of $(A_0-A_\infty)$ corresponds therefore to the actual amount of emeraldine base present in the film and the thicker the film is, the larger this value becomes. The results in FIG. 3 confirm this, as different $(A_0-A_\infty)$ values were obtained from the L2 (thin) film and the L4 (thick) film. In principle, thick films should be used to increase the upper limit on the measurement of ascorbic acid concentration. On the other hand, FIG. 3b shows that there was an inhibition effect in the initial response of thick films. This could be due to difficulty in wetting and percolation of thick films because of a different polymer morphology. The measurement sensitivity of thick films was reduced as a result.

Figure 4:
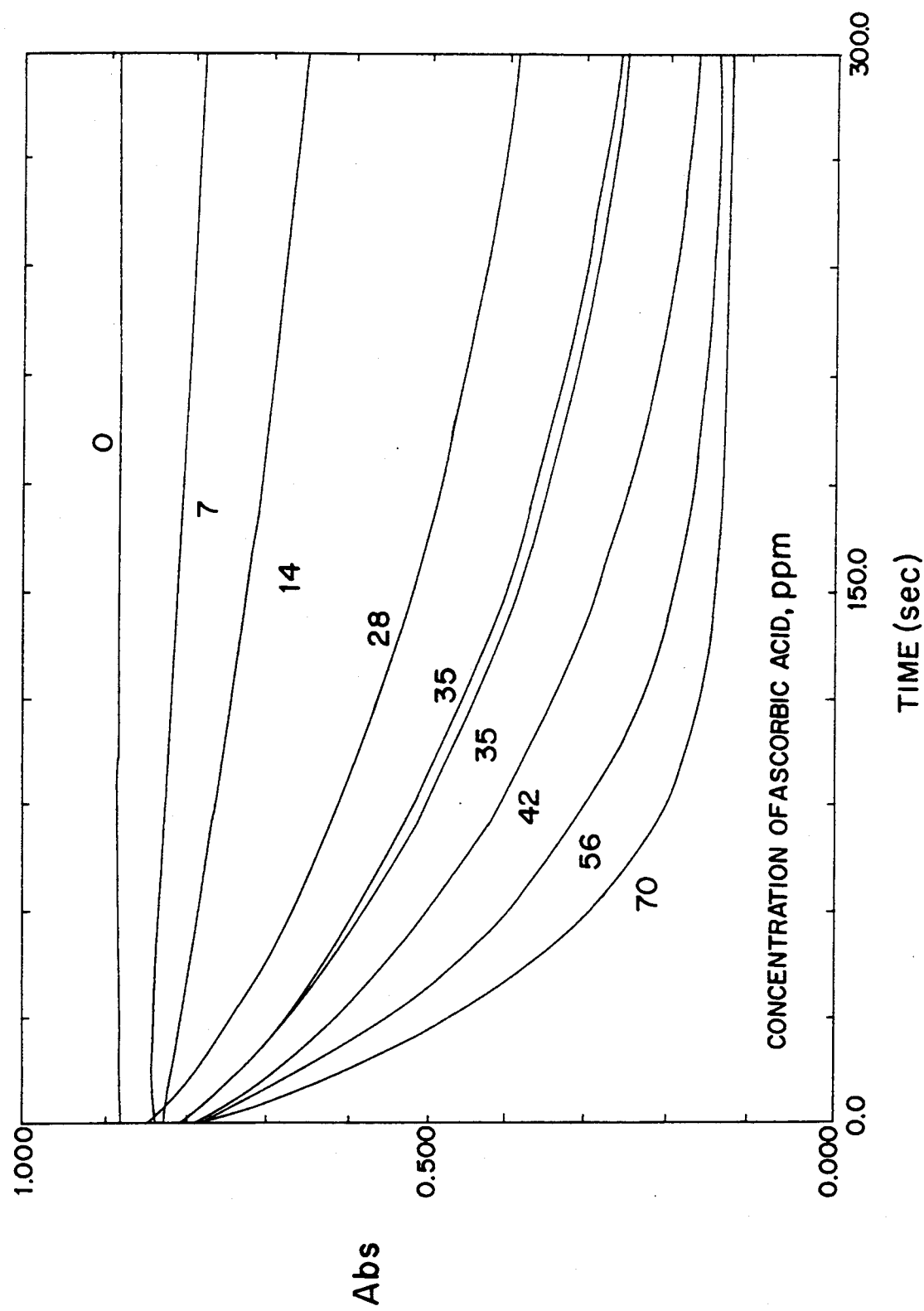
FIG. 4 shows the time course of UV/visible spectra of the chemically synthesized PAn film prepared in different concentrations of ascorbic acid.

The spectroscopic response at a wavelength of 625 nm of the chemically synthesized PAn film to changes in the ascorbic acid concentration was likewise similar (FIG. 4). The chemical synthesis is particularly suited for mass production because of its low manufacturing cost. Furthermore, films with nearly identical $A_0$ and $A_\infty$ values can be made by cutting a large, uniform PAn sheet into desired dimensions. As a result, only one calibration curve is needed for the ascorbic acid concentration determination, and this simplifies greatly the measurement process. This operational advantage was confirmed from experiments where reproducible and identical spectroscopic responses to 35 ppm ascorbic acid were obtained from two films cut from the same PAn sheet (FIG. 4). In short, the practicability of measurement of ascorbic acid concentration by the present method is greatly facilitated by the simplicity in fabrication and use of chemically synthesized PAn films.

Figure 5B:
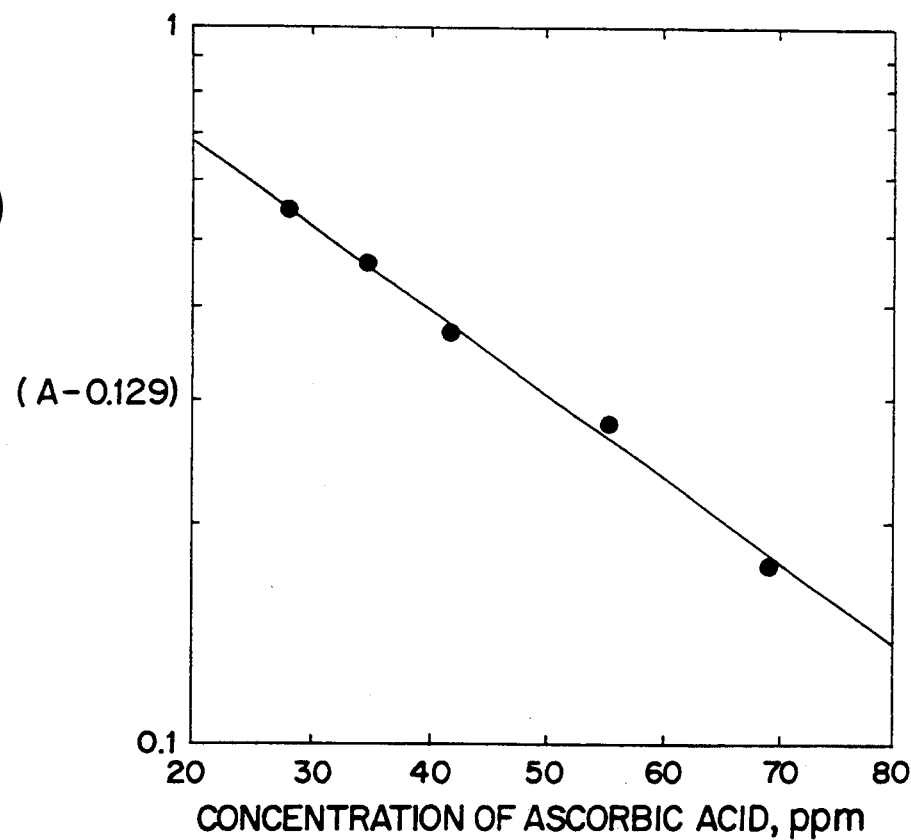
FIG. 5a and 5b show calibration curves of log-$(A-A_\infty)$ against ascorbic acid concentration for (a) L3 electrochemically deposited PAn film and (b) the chemically synthesized PAn film. The data were taken from FIGS. 2 and 4 respectively.
Figure 5A:
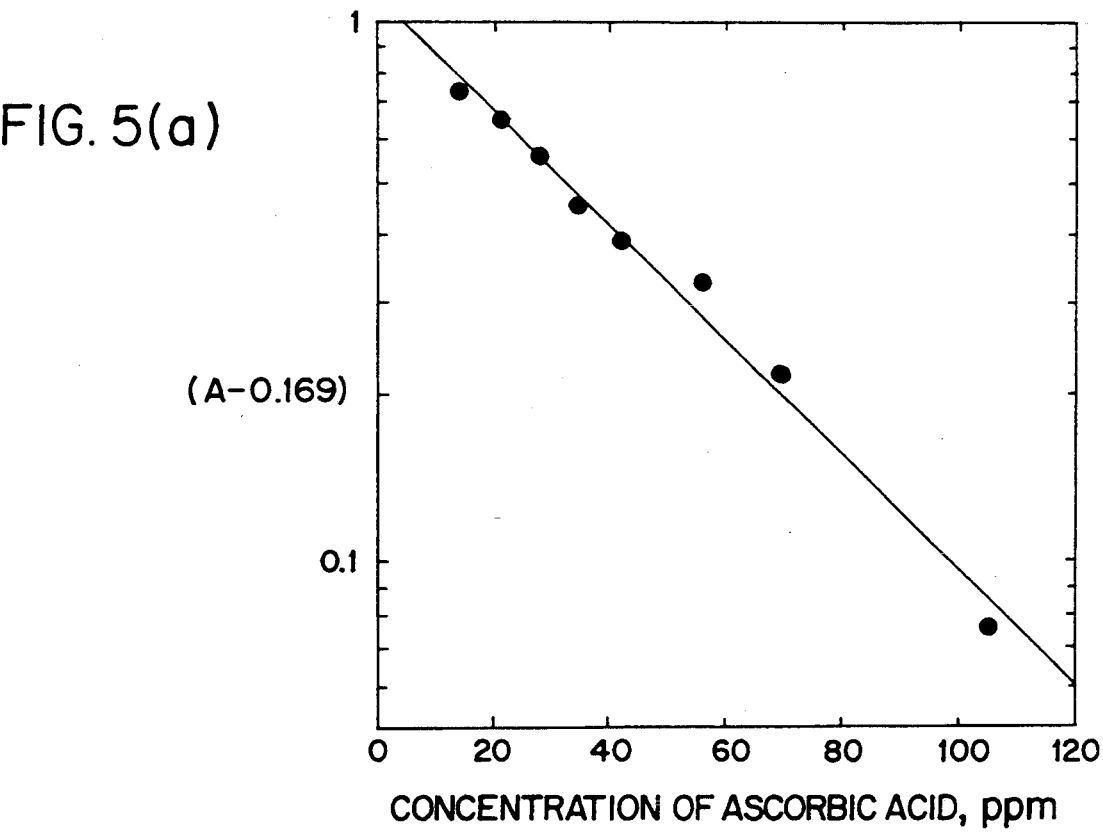

The results of FIG. 2 and FIG. 4 were used to generate plots of $\log(A-A_\infty)$ vs $[VC]^o$. Straight lines of good regression coefficients ($R^2=0.99$) were obtained from both electrochemically and chemically synthesized PAn films (FIG. 5). The absorbances (A) for both films were respectively taken at 50 seconds and 60 seconds. Similarly, a linear relationship was also found from the plots of $d\log(A-A_\infty)/dt$ against $[VC]^o$ (FIG. 6) for the same films. These demonstrate the validity of Equations [7] and [8] under the operating conditions suggested for the invention. On the other hand, some measurement inaccuracy for ascorbic acid concentrations lower than 28 ppm was evident in FIGS. 5 and 6. The inaccuracy was likely caused by slow diffusion of ascorbic acid within the film under a smaller concentration difference. The analysis of $\log(A-A_\infty)$ is an integral method, and as such is more direct and easier to apply than any method based on the measurement of differential quantities such as $d\log(A-A_\infty)/dt$. However, the experimental error in integral analysis could also be large if the reaction time is much shorter than the measurement time, which would be the case for very high concentrations of ascorbic acid. The disadvantages of measurement by $d\log(A-A_\infty)/dt$ lie obviously with the tedium of data differentiation and the susceptibility of differentiation to experimental noise. Furthermore, the slope is also distorted when the reaction is inhibited in the case of low concentration of ascorbic acid.

Figure 6A:
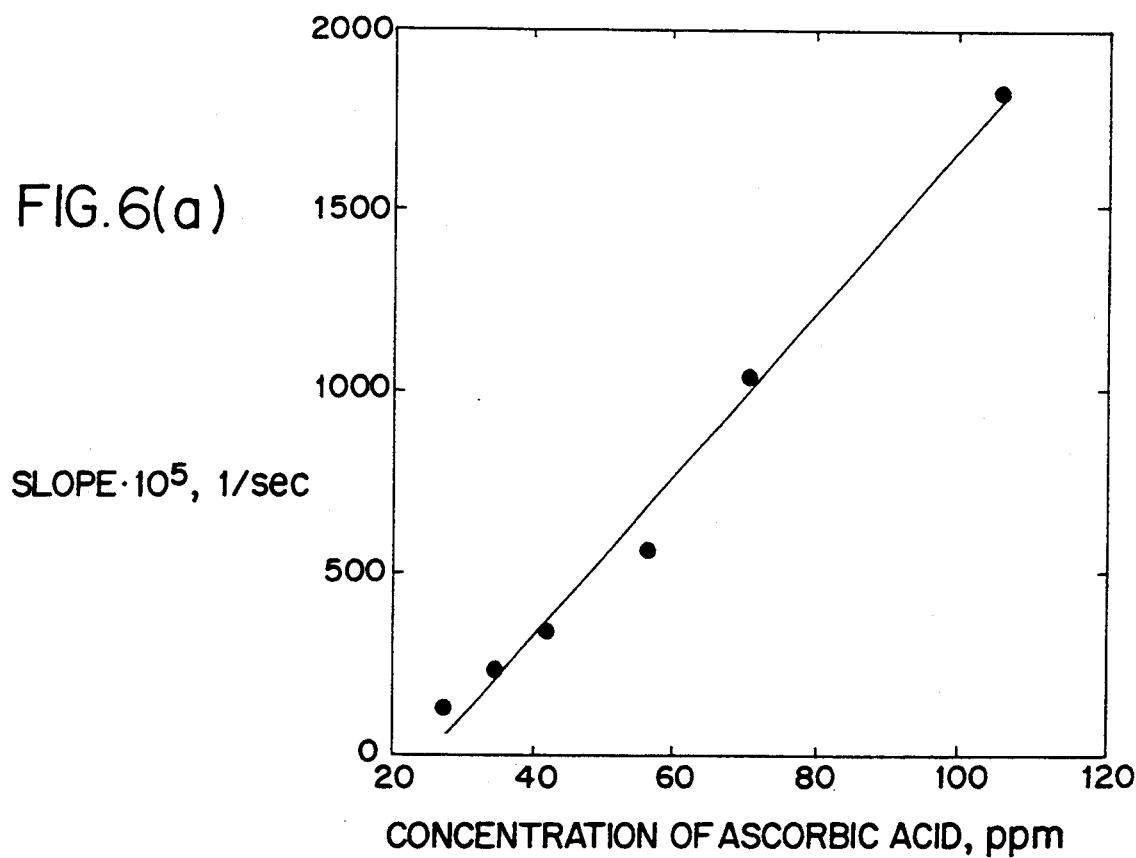
FIGS. 6a and 6b show calibration curves of dlog-$(A-A_\infty)/dt$ against ascorbic acid concentration for (a) L3 electrochemically deposited PAn film and (b) the chemically synthesized PAn film. The data were taken from FIGS. 2 and 4 respectively.
Figure 6B:
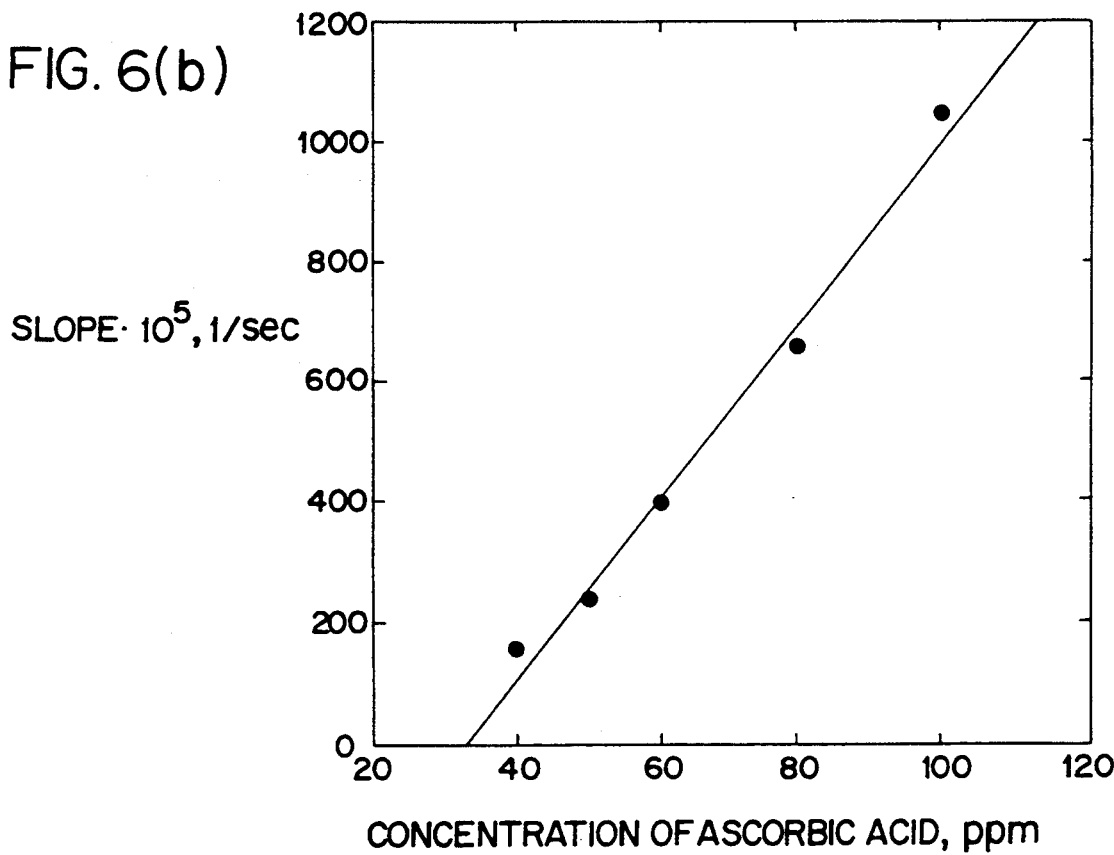
Figure 7A:
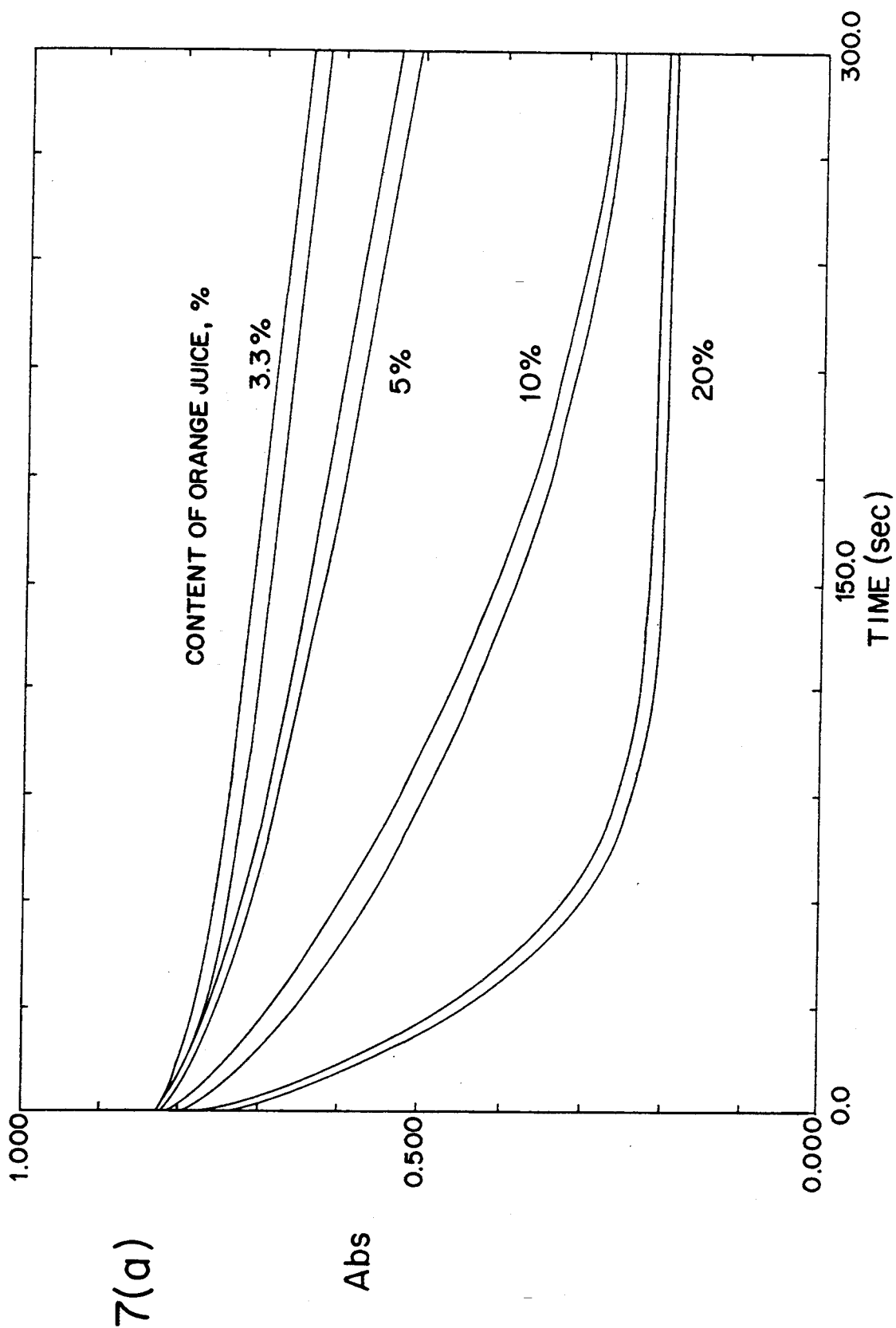
FIGS. 7a and 7b show the time course of UV/visible spectra of the chemically synthesized PAn film in different dilutions of (a) orange juice #1 and (b) watermelon juice #2.
Figure 7B:
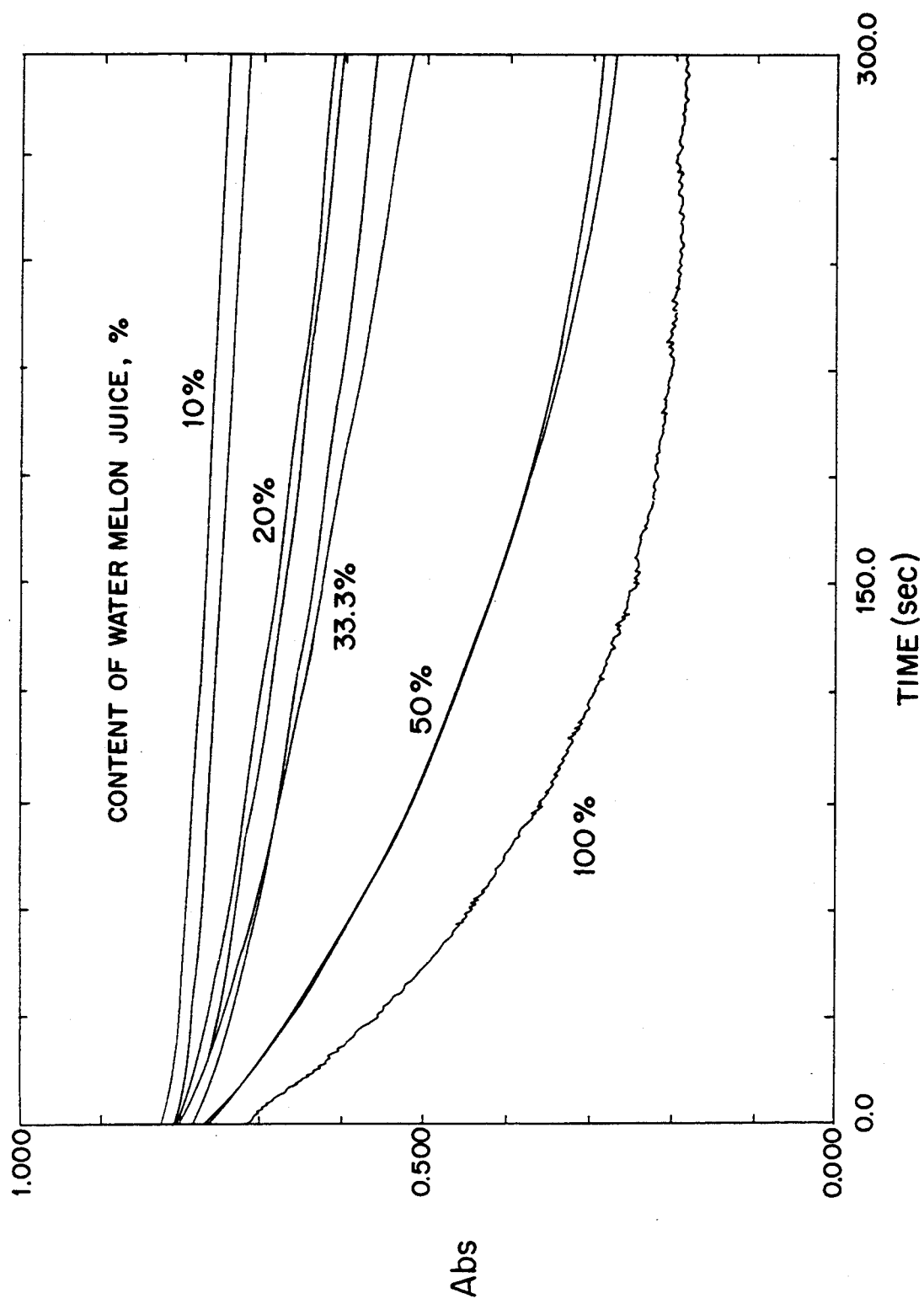
Figure 8A:
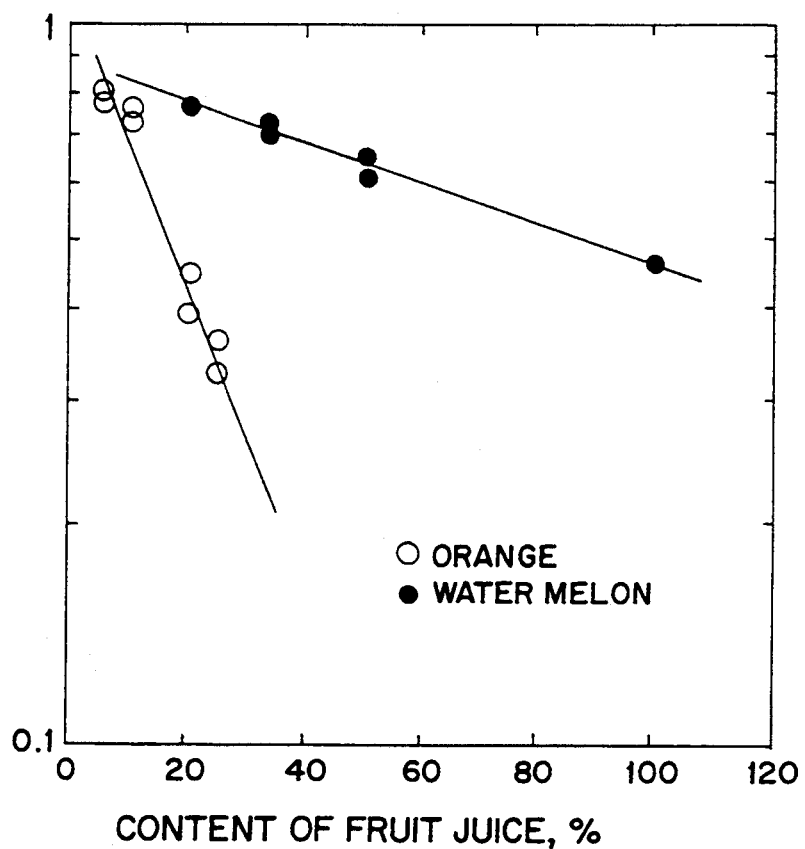
FIGS. 8a and 8b show a plot of $\log(A-A_\infty)$ against juice content for (a) L3 electrochemically deposited PAn film and (b) the chemically synthesized PAn film.
Figure 8B:
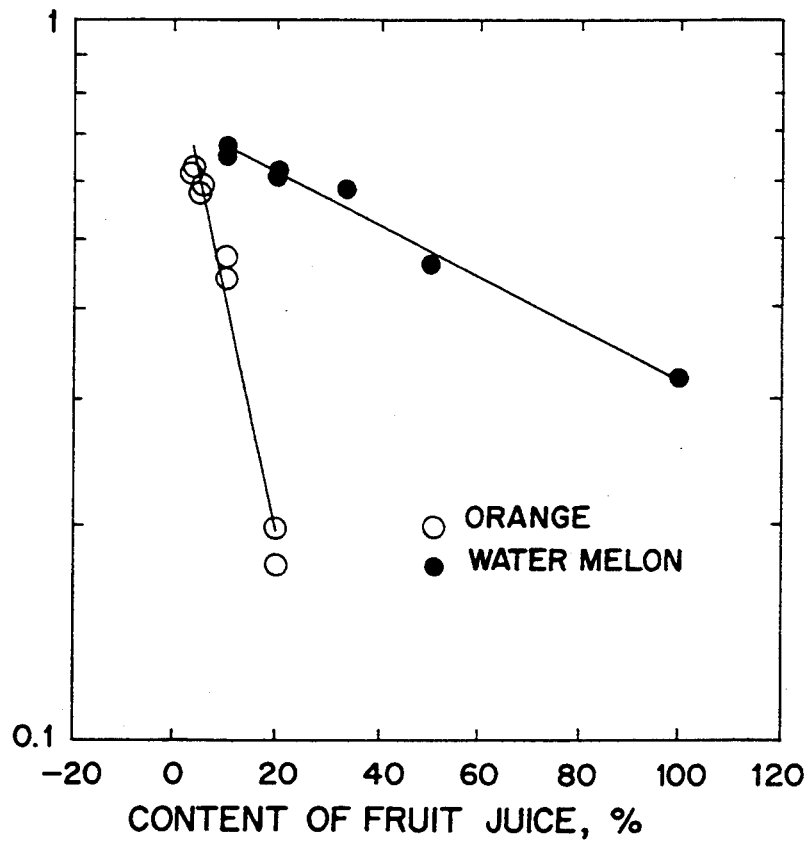

As a demonstration of the practicality of the present invention, the calibration curves in FIGS. 5 and 6 were used for the determination of ascorbic acid levels in fresh fruit juices. Fresh orange juice and fresh watermelon juice were prepared by squeezing the fruits, followed only by low-pressure separation without any further pretreatment. Prior to the measurements, the pure fruit juices were diluted with oxygen-free deionized water to different juice concentrations. In every spectroscopic measurement of a sample with a particular juice content, another aliquot of the same sample was also used as a reference in the spectrophotometer to eliminate any influence of the color of the fruit juice. On the other hand, a biological ascorbic acid assay kit from Boehringer Mannheim was used to compare the effectiveness of the present method against the biological method of ascorbic acid determination. Due to the rapid oxidation of ascorbic acid in fruit juices, the determination of ascorbic acid by the biological and the present methods had to be conducted simultaneously, in parallel experimental runs. FIG. 7 shows the time course of UV/vis spectra of the chemically synthesized PAn film in the presence of two fruit juices of different contents. The wavelength in the time course measurement was fixed at 625 nm. The repeatability of the measurement was considered as good, since the response curves in FIG. 7 were close to one another. The same conclusion also applied to the electrochemically synthesized film and the corresponding plots are therefore omitted here. The plot of $\log(A-A_\infty)$ against juice content in FIG. 8 follows the linear relationship in Equation [8], regardless of the origin of PAn synthesis and the type of fruit juice. The absorbances (A) ill FIG. 8 were taken at 60 seconds and 50 seconds for the chemically synthesized and the electrochemically synthesized films respectively, as required by the calibration curves in FIG. 5. Similarly, a linear relationship was also found between the slope, $d\log(A-A_\infty)/dt$, and the juice content in the context of Equation [7]. As a result, the calibration curves in FIGS. 5 and 6 can be used to determine the concentrations of ascorbic acid in orange juice and watermelon juice at any dilution by taking absorbance measurements at a fixed time, or by measurement of the slope $d\log(A-A_\infty)/dt$. Tables 1 and 2 list the results of such endeavors and also use the Boehringer test kit as a comparison. The relative standard deviations (R.S.D.) of less than 10% for both integral and differential analyses were considered satisfactory for measurements of biological samples. This shows that the two analytical methods based on the spectrophotometric response of PAn have the required reliability to determine ascorbic acid concentration. The exceptionally high R.S.D. of 20.5% in the differential analysis of watermelon #2 was due to the low ascorbic acid levels in the samples. Other than that, the measurements by this invention were in good agreement with that from the biological assay but without the requirement of long reaction time of the biological assay.

TABLE 1

| Determination of ascorbic acid in fruit juice samples using chemically synthesized PAn films | | | | | | | |
|---|---|---|---|---|---|---|---|
| Method | Integral Analysis | | | | Differential Analysis | | |
| Equation | $\log(A-0.129) = 0.0631 - 0.0114C$ | | | | Slope $\times 10^5 = .490 + 21.3C$ | | |
| Sample | Orange #1 | | Water-melon #1 | | Orange #1 | | Water-melon #1 |
| Dilution Ratio (D) | 5 | 10 | 2 | 3 | 5 | 10 | 2 | 3 |
| Abs. (A) at 60s | 0.326 | 0.600 | 0.586 | 0.717 | 826 | 243 | 227 | 74 |
| or Slope (b $\times 10^8$) | 0.304 | 0.569 | 0.584 | 0.709 | 887 | 252 | 224 | 76 |
| $C_{cal}$ | 67.4 | 34.2 | 35.4 | 25.8 | 61.7 | 34.4 | 33.6 | 26.4 |
| (ppm) | 71.9 | 36.8 | 35.5 | 26.3 | 64.6 | 34.8 | 33.5 | 26.5 |
| $C_{cal} \times D$ | 337.1 | 342.1 | 70.7 | 77.3 | 308.5 | 343.7 | 67.2 | 79.3 |
| (ppm) | 359.7 | 368.1 | 71.1 | 78.9 | 322.8 | 347.9 | 67.0 | 79.6 |

TABLE 1-continued

Determination of ascorbic acid in fruit juice samples using chemically synthesized PAn films

| Method | Integral Analysis | | | | Differential Analysis | | | |
|---|---|---|---|---|---|---|---|---|
| Equation | $\log(A-0.129) = 0.0631 - 0.0114C$ | | | | Slope $\times 10^5 = .490 + 21.3C$ | | | |
| Sample | Orange #1 | | Water-melon #1 | | Orange #1 | | Water-melon #1 | |
| Dilution Ratio (D) | 5 | 10 | 2 | 3 | 5 | 10 | 2 | 3 |
| $C_{ave}$ (ppm) | 350.8 | | 74.5 | | 330.7 | | 73.3 | |
| R.S.D.(%) (n = 4) | 4.1 | | 5.6 | | 5.6 | | 9.7 | |
| Boehringer test-kit (ppm) | 335 | | 70.4 | | 335 | | 70.4 | |

TABLE 2

Determination of ascorbic acid in fruit juice samples using electrodeposited PAn film (L3)

| Method | Integral Analysis | | | | Differential Analysis | | | |
|---|---|---|---|---|---|---|---|---|
| Equation | $\log(A-0.169) = 0.0418 - 0.0106C$ | | | | Slope $\times 10^5 = -568 + 22.27C$ | | | |
| Sample | Orange #2 | | Water-melon #2 | | Orange #2 | | Water-melon #2 | |
| Dilution Ratio (D) | 4 | 5 | 2 | 3 | 4 | 5 | 2 | 3 |
| Abs. (A) at 50s or Slope (b $\times 10^5$) | 0.532 | 0.619 | 0.819 | 0.899 | 662 | 491 | 53 | 31 |
| | 0.497 | 0.566 | 0.779 | 0.874 | 752 | 508 | 61 | 27 |
| $C_{cal}$ (ppm) | 45.5 | 36.7 | 21.6 | 16.8 | 55.2 | 47.6 | 27.9 | 26.9 |
| | 49.7 | 41.8 | 24.2 | 18.3 | 59.3 | 48.3 | 28.2 | 26.7 |
| $C_{cal} \times D$ (ppm) | 182.0 | 183.5 | 43.2 | 50.5 | 220.9 | 237.7 | 55.8 | 80.7 |
| | 198.6 | 209.1 | 48.4 | 54.8 | 237.1 | 241.6 | 56.5 | 80.2 |
| $C_{ave}$ (ppm) | 193.3 | | 49.2 | | 234.3 | | 68.3 | |
| R.S.D.(%) (n = 4) | 6.6 | | 9.7 | | 3.9 | | 20.5 | |
| Boehringer test-kit (ppm) | 212 | | 51 | | 212 | | 51 | |

TABLE 3

Interference of sulfite on the spectrophotometric response of chemically synthesized PAn in 50ppm of ascorbic acid

| Methods | Integral Analysis | | | | Differential Analysis | | | |
|---|---|---|---|---|---|---|---|---|
| Equation | $\log(A-0.129) = 0.0631 - 0.0114C$ | | | | $b \times 10^5 = -490 + 21.3C$ | | | |
| Sulfite added (ppm) | 0 | 5 | 10 | 20 | 0 | 5 | 10 | 20 |
| Abs. (A) at 60s or Slope (b $\times 10^8$) | 0.443 | 0.420 | 0.405 | 0.460 | 614 | 701 | 769 | 516 |
| $C_{cal}$ (ppm) | 49.6 | 52.6 | 54.6 | 47.7 | 51.8 | 55.9 | 59.1 | 47.2 |
| Relative error (%) | 0.8 | 5.2 | 9.2 | 4.6 | 3.6 | 11.8 | 18.2 | 5.6 |

Figure 9:
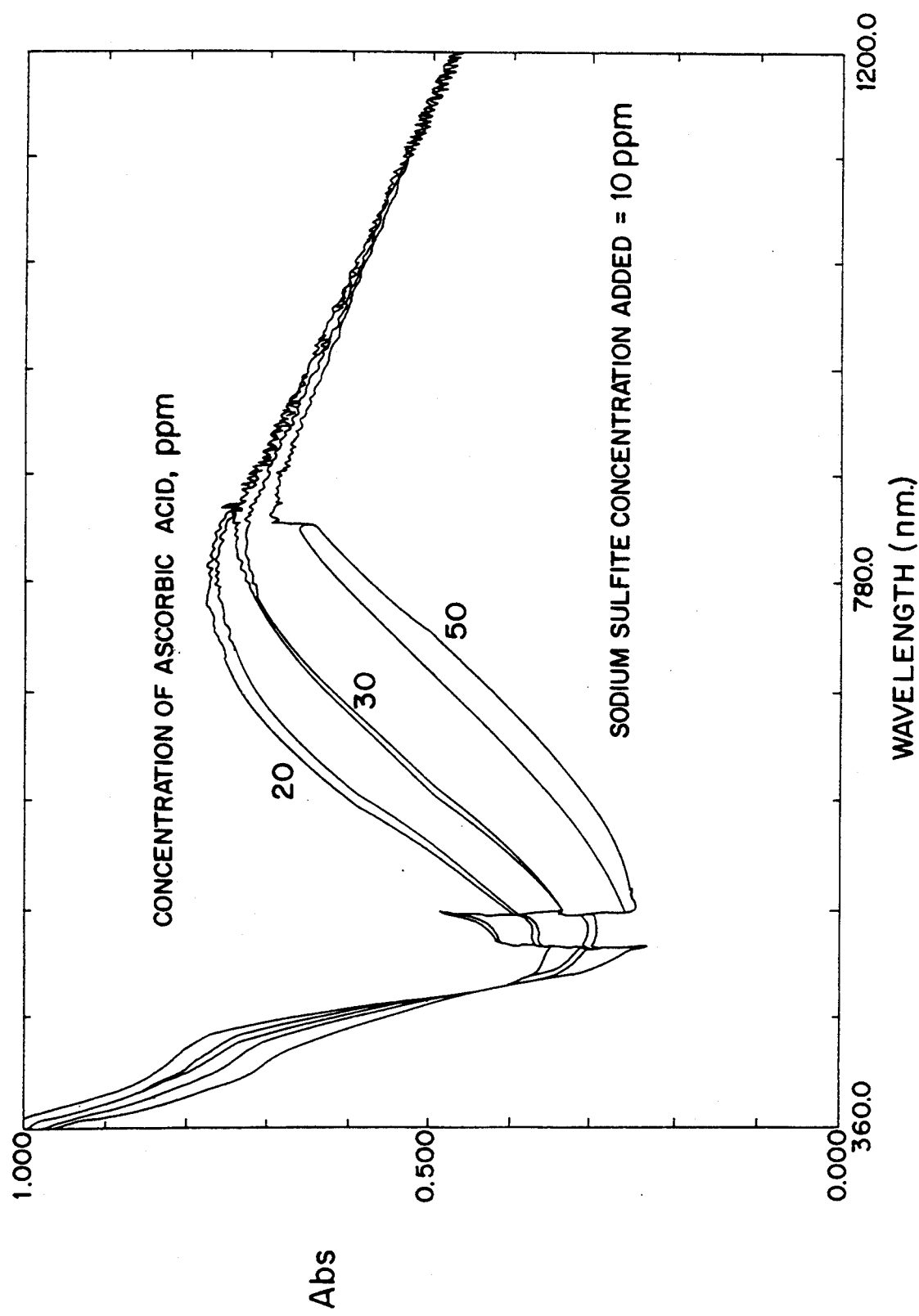
FIG. 9 shows UV/visible spectra of the chemically synthesized PAn film in different concentrations of ascorbic acid with and without 10 ppm of sodium sulfite.

Sulfite is a common antioxidant in food, and as such is a potential interferant in the determination of ascorbic acid. FIG. 9 shows the UV/visible spectra of chemically synthesized PAn film in various ascorbic acid concentrations with and without the presence of 10 ppm of sodium sulfite. The presence of sulfite hardly altered the major spectrophotometric features of PAn in solutions where the sulfite to ascorbic acid ratios were 1:5, 1:3 and 1:1 respectively. In view of the fact that the sulfite to ascorbic acid ratio in packaged juices is usually less than 1:10, the interference effect of sulfite in the spectrophotometric response of PAn is negligible. Nevertheless, a quantitative assessment of the extent of interference was also carried out.

Figure 10:
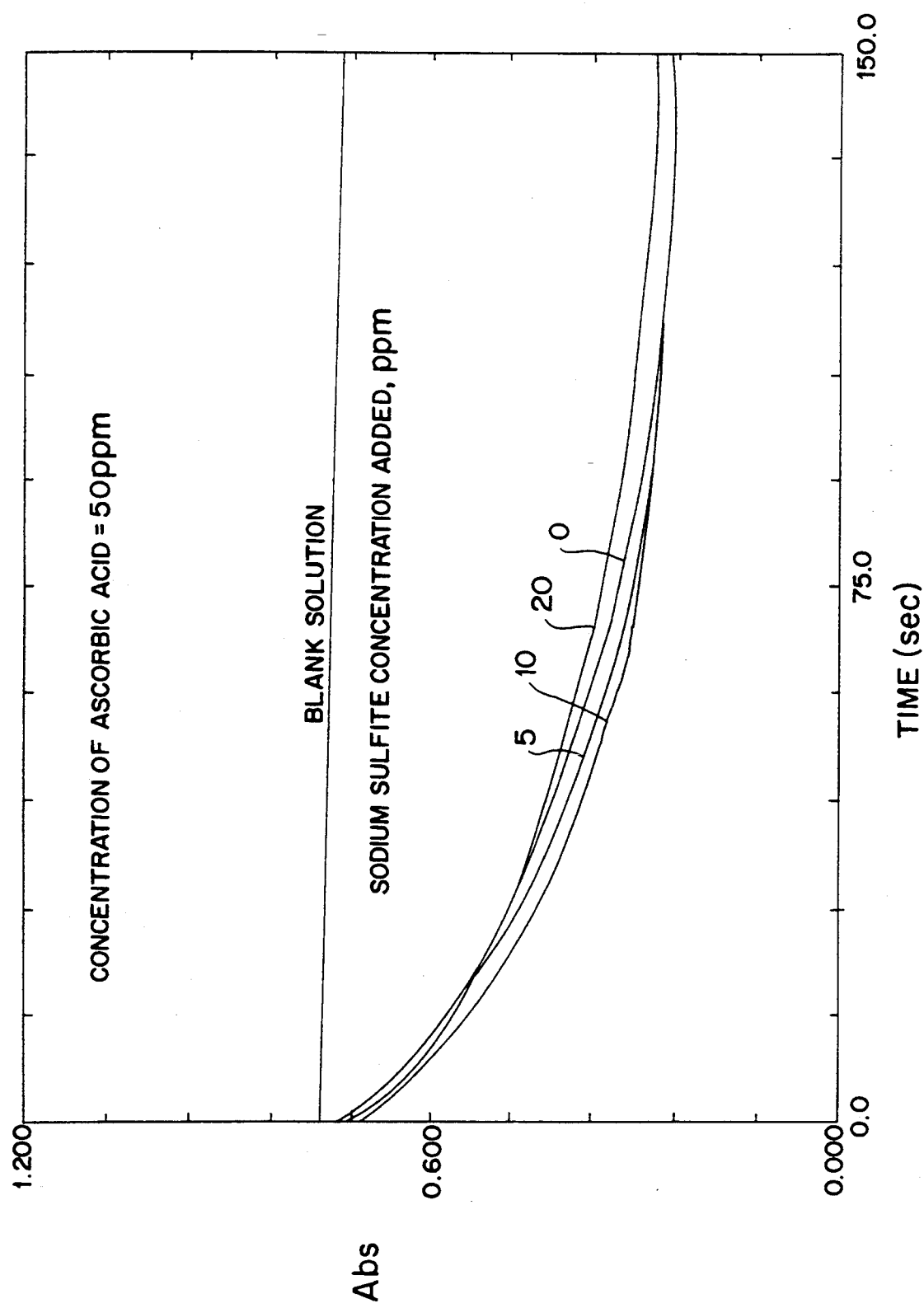
FIG. 10 shows the time course of UV/visible spectra of the chemically synthesized PAn film in 50 ppm of ascorbic acid in the presence of different concentrations of sodium sulfite.

FIG. 10 shows the time course spectra of PAn in 50 ppm ascorbic acid with the addition of various concentrations of sulfite. The effect of sulfite addition was analyzed in terms of the calibration equations in Table 1 that are of relevance to the chemically synthesized PAn film. The results of such analysis for both integral and differential methods of measurements are presented in Table 3. The calculated concentrations of ascorbic acid in the blank solution from integral and differential analyses were 49.6 ppm and 51.8 ppm respectively, and were very close to the true concentration of 50 ppm. In 50 ppm ascorbic acid solutions, the maximum relative errors were 9.2% for the former and 18.2% for the latter, respectively. Increasing the sulfite concentration to 20 ppm did not result in a proportional increase in error, indicating that reduction of PAn by sulfite was much less than that by ascorbic acid. The selectivity of spectrophotometric measurement of PAn reduction by either integral or differential analysis is therefore satisfactory for ordinary applications, and the interference effect of sulfite in such measurements can be safely ignored.

The response from the chemically synthesized film is not substantially affected by the sulfite addition. The same film retained sufficient activity to be used for at least 50 measurements. This attests to the durability of the sensor material in the measurement of ascorbic acid according to this invention.

This invention is based on the spectrophotometric response of PAn reduction by ascorbic acid to determine the concentration of the latter. The method is quick in comparison to existing analytical procedure, and has adequate selectivity to disregard sulfite interference in practical samples. Example applications from this invention include the critical examination of ascorbic acid levels in clinical samples (urine, blood, etc.), and of checking the freshness of foods (fruits, vegetables, meat, etc.). The sensor material, namely, thin film PAn, can be synthesized electrochemically or chemically. The latter preparatory route is more cost effective, and produces PAn films of nearly identical properties that can be described by a single calibration curve provided by the manufacturer. The analysts are therefore relieved of the necessity of conducting calibration runs themselves.

A spectrophotometer is not necessary if the following practice is adopted. The change in the absorbance value $(A-A_\infty)$ in spectrophotometric measurements, brought about by the complete reduction of PAn by ascorbic acid, also corresponds to a change in PAn color from blue to light-yellow. The time taken for PAn to undergo such a color change is a function of both the film thickness and the ascorbic acid concentration. There would also be a direct correspondence between the film thickness and the ascorbic acid concentration should the transition of color be completed at a specific time. PAn films of different thicknesses can then be made so that they would produce the necessary color change for different concentrations of ascorbic acid at a given time. If the films are labelled with the concentrations they are calibrated against, they can be used in the same manner as the paper indicators in the pharmaceutical industry.

Figure 11A:
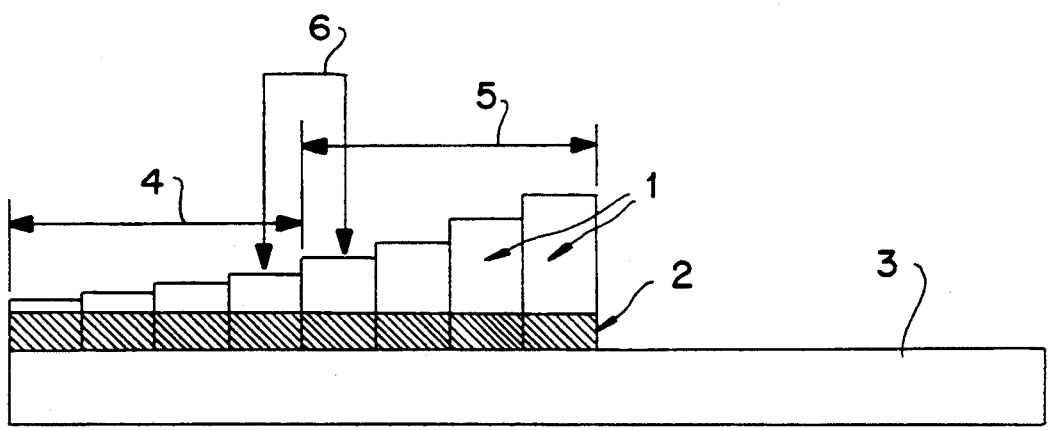
FIGS. 11A and 11B are diagrams (not to scale) showing two embodiments of test strips for use in visually determination of reductant or oxidant concentration.

For example, as shown in FIG. 11A, PAn films 1 of varying thicknesses are produced and assembled on a strip of substrate 2 in a sample holder 3. Previously, the PAn films have been calibrated against known reductant concentrations. The lowest reductant concentration that would cause a color change in a given thickness of film in a given time is noted as the calibrated standard or reference concentration value for that film. The test strip is immersed in the sample containing a reductant. After a prescribed time, the area of color change 4, and the area of lack of color change 5, are noted. The transition area 6 gives an indication of reductant concentration, since said reductant concentration will be within the calibrated values for the two films comprising the transition area.

Figure 11B:
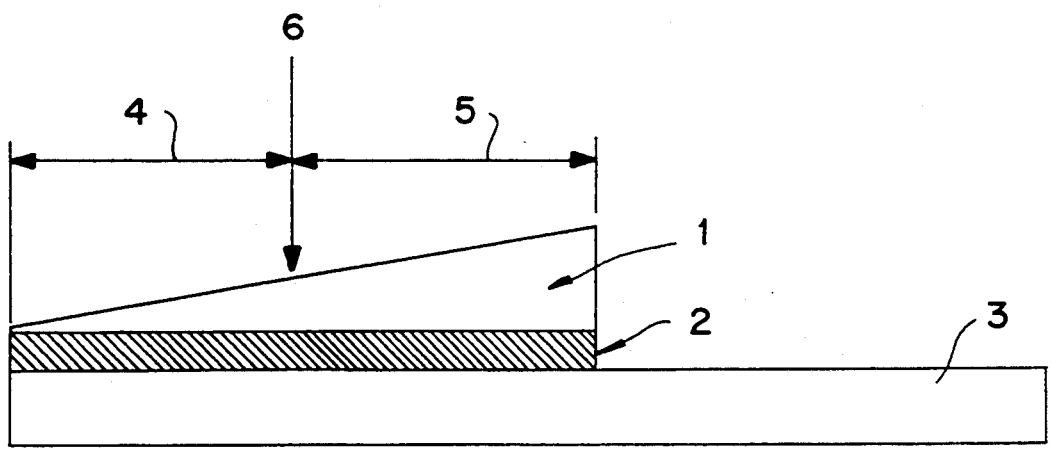

In FIG. 11B, the varying thicknesses of PAn film are provided by a wedge-shaped PAn film 1, provided on a strip of substrate 2 in a sample holder 3. The transition point 6 between the area of color change 4, and the area of lack of color change 5, indicates the reductant concentration.

This visual determination process is carried out analogously when the object of determination is oxidant concentration.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for determining the presence of a reductant in a liquid sample, comprising contacting said sample with a polyaniline in a partially oxidized state, reducing said polyaniline to a lower oxidation state, measuring the color change of said polyaniline accompanying said reduction, and determining the concentration of reductant present based upon said color change.

2. The method according to claim 1, wherein said reductant is ascorbic acid.

3. The method according to claim 1, wherein said polyaniline in a partially oxidized state is emeraldine.

4. The method according to claim 1, wherein said polyaniline in a lower oxidation state is leucoemeraldine.

5. The method according to claim 1, wherein said measuring of said color change comprises spectrophotometric analysis of said color change.

6. The method according to claim 5, wherein said measuring of said color change comprises ultraviolet/visible light spectrophotometric analysis.

7. The method according to claim 1, wherein said measuring of said color change comprises determining the time for a given thickness of polyaniline film to undergo a predetermined color change.

8. The method according to claim 1, wherein said sample comprises sulfites.

9. The method according to claim 1, wherein said sample is selected from the group consisting of urine samples, blood samples, and food samples.

10. The method according to claim 9, wherein said sample is a sample of fruit juice.

11. A method for determining the presence of an oxidant in a liquid sample, comprising contacting said sample with a polyaniline in a reduced state, oxidizing said polyaniline to a higher oxidation state, measuring the color change of said polyaniline accompanying said oxidation, and determining the concentration of said oxidant present based upon said color change.

12. The method according to claim 11, wherein said polyaniline in a reduced state is leucoemeraldine, and said polyaniline in a higher oxidation state is emeraldine.

13. The method according to claim 1, wherein:
said contacting comprises providing various thickness of polyaniline film on a test strip, for which the minimum reductant concentration to cause a color change in a given time is known, and immersing said test strip in a sample containing said reductant;
said reducing comprises maintaining said immersion for said given time; and
said determining of reductant concentration comprises visually observing the thickness or thicknesses of film wherein a transition from color change to lack of color change occurs.

14. The method according to claim 11, wherein:
said contacting comprises providing various thickness of polyaniline film on a test strip, for which the minimum oxidant concentration to cause a color change in a given time is known, and immersing said test strip in a sample containing said oxidant;
said oxidizing comprises maintaining said immersion for said given time; and
said determining of oxidant concentration comprises visually observing the thickness or thicknesses of film wherein a transition from color change to lack of color change occurs.

* * * * *